(12) United States Patent
Ishino et al.

(10) Patent No.: US 8,248,087 B2
(45) Date of Patent: Aug. 21, 2012

(54) LIQUID CONCENTRATION MEASURING DEVICE

(75) Inventors: Hirotsugu Ishino, Toyokawa (JP); Jun Tarui, Kariya (JP)

(73) Assignee: Denso Corporation, Kariya (JP)

( * ) Notice: Subject to any disclaimer, the term of this patent is extended or adjusted under 35 U.S.C. 154(b) by 430 days.

(21) Appl. No.: 12/406,446

(22) Filed: Mar. 18, 2009

(65) Prior Publication Data

US 2009/0251126 A1 Oct. 8, 2009

(30) Foreign Application Priority Data

Apr. 4, 2008 (JP) ................................. 2008-98217
Dec. 4, 2008 (JP) ................................. 2008-310117

(51) Int. Cl.
*G01R 27/08* (2006.01)
(52) U.S. Cl. ........ 324/693; 324/663; 324/674; 324/681; 324/686; 324/425; 324/442; 324/698; 324/722; 73/61.41; 73/61.43
(58) Field of Classification Search .................. 324/663, 324/674, 681, 686, 693, 425, 442, 698, 722; 73/61.41, 61.43
See application file for complete search history.

(56) References Cited

U.S. PATENT DOCUMENTS

| | | | | |
|---|---|---|---|---|
| 3,019,651 A | * | 2/1962 | Hermanson | 73/304 C |
| 3,950,237 A | * | 4/1976 | Arawa et al. | 204/405 |
| 4,042,465 A | * | 8/1977 | Morong et al. | 205/782 |
| 4,375,672 A | * | 3/1983 | Kato et al. | 701/102 |
| 4,383,221 A | * | 5/1983 | Morey et al. | 324/439 |
| 4,701,713 A | * | 10/1987 | Eaton et al. | 324/442 |
| 4,939,467 A | * | 7/1990 | Nogami et al. | 324/663 |
| 5,033,293 A | * | 7/1991 | Honma et al. | 73/114.38 |
| 5,187,444 A | * | 2/1993 | Kumada et al. | 324/663 |
| 5,202,637 A | * | 4/1993 | Jones | 324/425 |
| 5,231,358 A | * | 7/1993 | Kapsokavathis et al. | 324/672 |
| 5,234,666 A | * | 8/1993 | Suzuki | 422/82.09 |
| 5,239,268 A | * | 8/1993 | Moriguchi | 324/425 |
| 5,260,663 A | * | 11/1993 | Blades | 324/442 |
| 5,270,663 A | * | 12/1993 | Sano et al. | 324/676 |
| 5,313,168 A | * | 5/1994 | Ogawa | 324/663 |
| 5,334,940 A | * | 8/1994 | Blades | 324/442 |

(Continued)

FOREIGN PATENT DOCUMENTS

JP 05-099878 4/1993

(Continued)

OTHER PUBLICATIONS

Japanese Office Action dated Nov. 19, 2009, issued in corresponding Japanese Application No. 2008-310117, with English translation.

(Continued)

*Primary Examiner* — Patrick Assouad
*Assistant Examiner* — Lamarr Brown
(74) *Attorney, Agent, or Firm* — Nixon & Vanderhye P.C.

(57) ABSTRACT

A liquid concentration measuring device has first and second switches, which are turned on and off at two frequencies. When the first switch is turned on and the second switch is turned off, a detection electrode pair is charged. When the first switch is turned off and the second switch is turned on, the positive side of the detection electrode pair is grounded so that the charged detection electrode pair discharges. The difference between the output voltages of an amplifier produced by charging and discharging the detection electrode pair at the two frequencies is used to determine an alcohol concentration in gasoline.

20 Claims, 11 Drawing Sheets

U.S. PATENT DOCUMENTS

| | | | | |
|---|---|---|---|---|
| 5,337,018 | A * | 8/1994 | Yamagishi | 324/693 |
| 5,361,035 | A * | 11/1994 | Meitzler et al. | 324/663 |
| 5,367,264 | A * | 11/1994 | Brabetz | 324/674 |
| 5,418,465 | A * | 5/1995 | Seipler et al. | 324/663 |
| 5,457,396 | A * | 10/1995 | Mori et al. | 324/724 |
| 5,465,700 | A * | 11/1995 | Nishimoto | 123/492 |
| 5,521,515 | A * | 5/1996 | Campbell | 324/674 |
| 5,592,098 | A * | 1/1997 | Suzuki et al. | 324/663 |
| 5,594,163 | A * | 1/1997 | Suzuki | 73/61.44 |
| 5,708,363 | A * | 1/1998 | Yates et al. | 324/442 |
| 5,869,758 | A * | 2/1999 | Huiberts | 73/197 |
| 6,057,693 | A * | 5/2000 | Murphy et al. | 324/663 |
| 6,127,441 | A * | 10/2000 | Sakamoto et al. | 521/91 |
| 6,842,017 | B2 * | 1/2005 | McKenzie et al. | 324/663 |
| 6,885,199 | B2 * | 4/2005 | Desmier et al. | 324/663 |
| 6,927,583 | B2 * | 8/2005 | Vanzuilen et al. | 324/686 |
| 7,378,857 | B2 * | 5/2008 | Franke et al. | 324/663 |
| 7,406,871 | B2 * | 8/2008 | Sugiura | 73/592 |
| 7,735,354 | B2 * | 6/2010 | Yamamoto et al. | 73/61.41 |
| 2002/0022668 | A1 * | 2/2002 | Welsh et al. | 514/738 |
| 2002/0040593 | A1 * | 4/2002 | Schaefer et al. | 73/61.43 |
| 2002/0056310 | A1 * | 5/2002 | Hada et al. | 73/23.32 |
| 2004/0120418 | A1 * | 6/2004 | Pasternak et al. | 375/272 |
| 2004/0169545 | A1 * | 9/2004 | Aiba et al. | 327/530 |
| 2004/0187570 | A1 * | 9/2004 | Williamson | 73/304 C |
| 2004/0199131 | A1 * | 10/2004 | Kitamura | 604/318 |
| 2005/0057267 | A1 * | 3/2005 | Nicholson et al. | 324/698 |
| 2005/0093556 | A1 * | 5/2005 | Mueller et al. | 324/693 |
| 2007/0234820 | A1 * | 10/2007 | Yamamoto | 73/861.12 |
| 2008/0053404 | A1 * | 3/2008 | Mizuno et al. | 123/406.19 |
| 2009/0051373 | A1 * | 2/2009 | Kato et al. | 324/693 |
| 2009/0100911 | A1 * | 4/2009 | Kawanishi et al. | 73/61.43 |
| 2009/0157345 | A1 * | 6/2009 | Yoshioka et al. | 702/136 |
| 2009/0212788 | A1 * | 8/2009 | Patterson | 324/601 |
| 2009/0320567 | A1 * | 12/2009 | Takahashi et al. | 73/53.07 |
| 2010/0108507 | A1 * | 5/2010 | Tarui | 204/402 |

FOREIGN PATENT DOCUMENTS

| | | |
|---|---|---|
| JP | 6-3313 | 1/1994 |
| JP | 09-318575 | 12/1997 |

OTHER PUBLICATIONS

U.S. Appl. No. 12/311,312, Takahashi et al, filed Mar. 26, 2009.

Office Action (5 pgs.) dated Nov. 28, 2011 issued in corresponding Chinese Application No. 200910132917.6 with an at least partial English-language translation thereof.

* cited by examiner

FIG. 5A        FIG. 5B
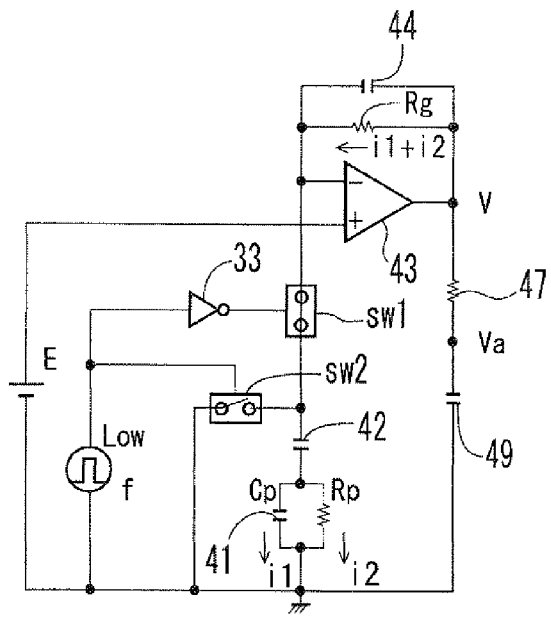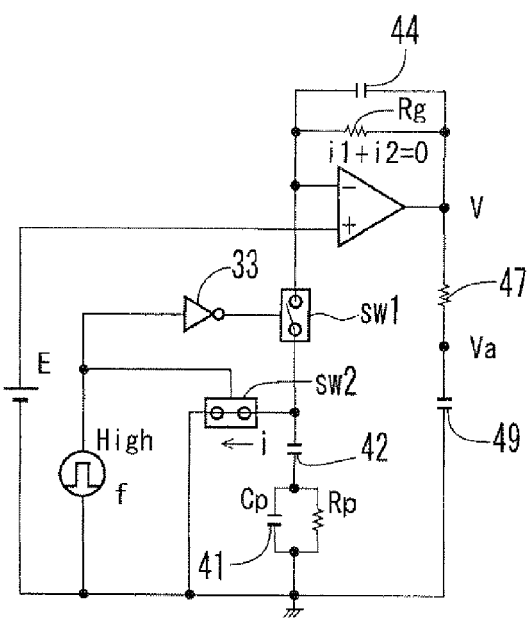
FIG. 6
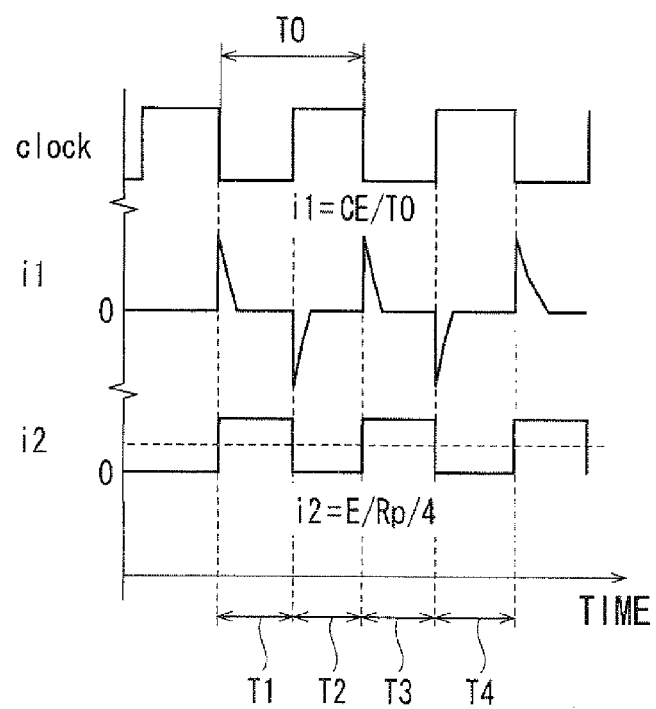

LIQUID CONCENTRATION MEASURING DEVICE

CROSS REFERENCE TO RELATED APPLICATION

This application is based on and incorporates herein by reference Japanese Patent Applications No. 2008-98217 filed on Apr. 4, 2008 and No. 2008-310117 filed on Dec. 4, 2008.

FIELD OF THE INVENTION

The present invention relates to a liquid concentration measuring device.

BACKGROUND OF THE INVENTION

As low pollution fuel for vehicles, alcohol-mixed gasoline is used recently. The most appropriate air-fuel ratio of such mixed gasoline is different from that of gasoline itself. It is therefore essential to measure the amount of alcohol in the mixed gasoline, that is, the alcohol concentration in the mixed gasoline.

For measuring the alcohol concentration with high precision, it is preferred to use a parameter (physical constant), which has a relatively high change rate. For this reason, it is proposed to measure changes in the specific inductive capacity. Since the specific inductive capacity is calculated based on the change in the electrostatic capacity, JP 6-3313A, for example, proposes a liquid concentration measuring device, which has a pair of detection electrodes (detection electrode pair) provided to face each other to measure the static electric capacity. This liquid concentration measuring device further has a change-over switch and an electronic control circuit. The detection electrode pair is charged and discharged repeatedly at a fixed frequency by the control circuit through the change-over switch, so that a detection output voltage is produced in proportion to the concentration of liquid to be measured.

If the capacitance is measured by using the detection electrode pair, the resistance (leak resistance) between the electrodes becomes relatively smaller as the gasoline contains more impurities, that is, as the gasoline is of lower quality. Specifically, if the gasoline contains no impurities, it is in the insulated condition resulting in that the leak resistance becomes infinite and the conductivity between the electrodes becomes substantially zero. If the impurities increase, the conductivity becomes relatively high.

It is thus necessary to remove influence of the leak resistance to measure the concentration of liquid such as alcohol precisely.

It is therefore an object of the present invention to provide a liquid concentration measuring device, which can measure a liquid concentration without being influenced by a leak resistance developed in a detection electrode pair.

According to one aspect of the present invention, a liquid concentration measuring device comprises a detection electrode pair, a switch section, an operation signal outputting section and a measured value outputting section. The detection electrode pair includes a pair of electrodes facing each other and disposed in a liquid to be measured. The switching section is provided to switch over charging and discharging of the detection electrode pair. The operation signal outputting section is configured to produce operation signals of a predetermined frequency to control switching operation of the switching section at a predetermined period. The measured value outputting section is configured to produce a voltage for charging the detection electrode pair through the switching section and to produce a detection voltage corresponding to a static electric capacity of the detection electrode pair. The operation signal outputting section is configured to produce a first operation signal of a first frequency and a second operation signal of a second frequency for operating the switching section at a first period and a second period, respectively. The measured value outputting section is configured to produce a first detection voltage and a second detection voltage when the switching section is operated at the first frequency and the second frequency, respectively.

BRIEF DESCRIPTION OF THE DRAWINGS

The above and other objects, features and advantages of the present invention will become more apparent from the following description made with reference to the accompanying drawings. In the drawings:

FIGS. 5A and 5B are circuit diagrams showing a circuit, in which a coupling capacitor is provided;

FIG. 6 is a time chart showing currents that flow in a detection electrode pair and a leak resistance in case that a coupling capacitor is provided;

DETAILED DESCRIPTION OF THE PREFERRED EMBODIMENT

Figure 1:
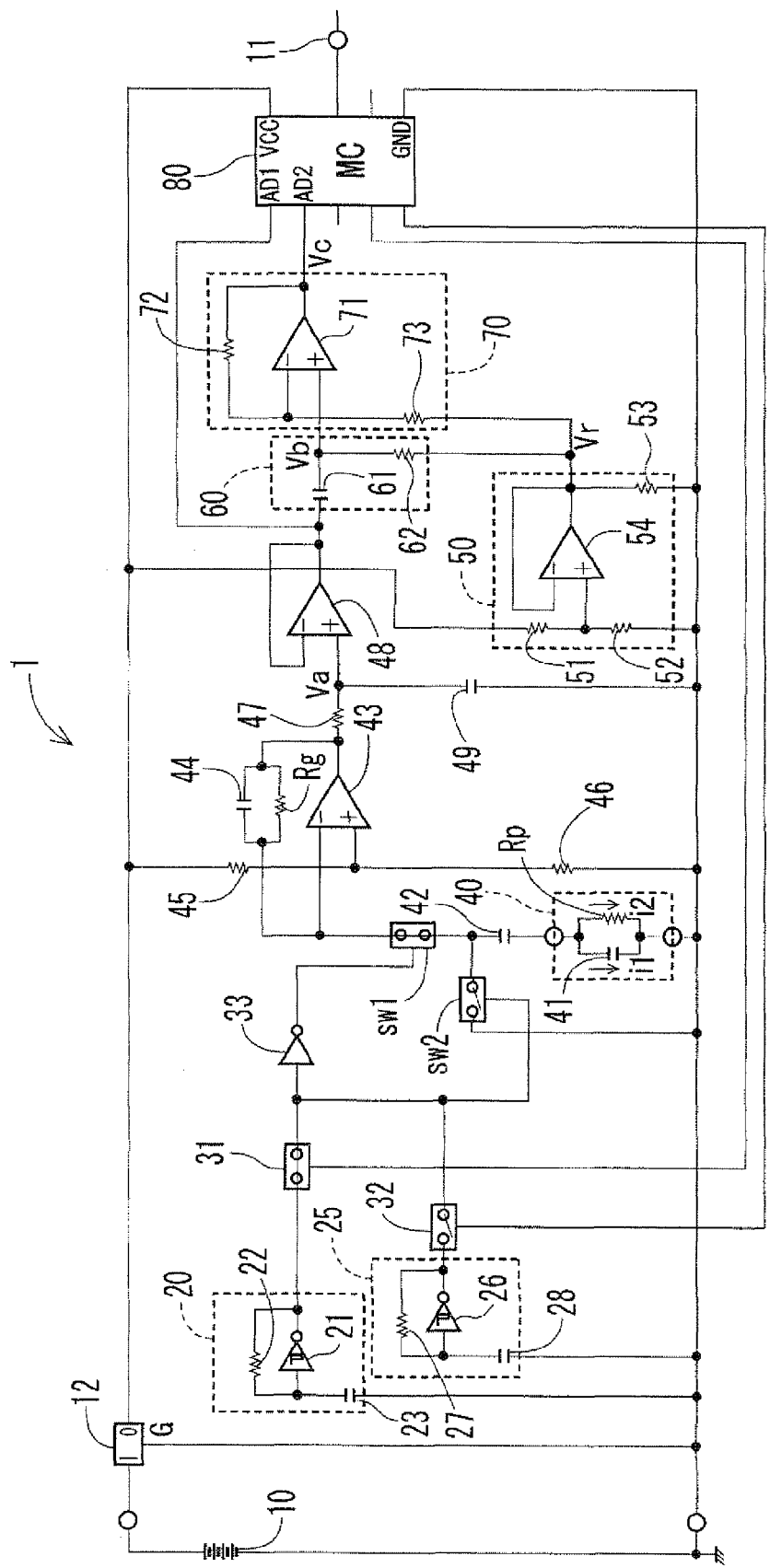
FIG. 1 is a circuit diagram showing an alcohol concentration measuring device according to the first embodiment of the present invention.

The present invention will be described in more detail with reference to various embodiments, in which the same or similar parts are denoted with the same or similar reference numerals thereby to eliminate the same or similar description.

(First Embodiment)

Referring first to FIG. 1, an alcohol concentration measuring device 1 is configured to measure the concentration of ethanol in gasoline and mounted in a vehicle. The alcohol concentration measuring device 1 is operable with an electric power voltage Vcc (e.g., 5V) of a battery 10 and produces an output voltage indicating a measured result at an output terminal 11. The voltage Vcc is stably supplied by a voltage regulator IC (three-terminal regulator) as a voltage source 12.

The alcohol concentration measuring device 1 is configured with a first oscillator circuit 20, a second oscillator circuit 25, a detector 40, a reference voltage generator circuit 50, an AC coupler circuit 60, an amplifier circuit 70 and a microcomputer 80.

The first oscillator circuit 20 includes a Schmidt trigger 21 having a hysteresis characteristic, a resistor 22 connected in parallel to the Schmidt trigger 21 and a capacitor 23 connected between the input side of the Schmidt trigger 21 and the ground. With this configuration, the first oscillator circuit 20 produces a first pulse signal (clock) as a first operation signal at a first fixed frequency f1. Similarly, the second oscillator circuit 25 includes a Schmidt trigger 26, a resistor 27 and a capacitor 28. With this configuration, the second oscillator circuit 25 produces a second pulse signal (clock) as a second operation signal at a second fixed frequency f2, which is lower than the first fixed frequency. The Shmidt triggers 21 and 26 may be replaced with any other circuits, which produce the similar operation signals.

The output terminals of the first oscillator circuit 20 and the second oscillator circuit 25 are connected to a first frequency change-over switch 31 and a second frequency change-over switch 32, respectively. The frequency change-over switches 31 and 32 are controlled by the microcomputer 80 to turn on alternately. As a result, the subsequent circuits operate with the operation signal of either one of the frequencies f1 and f2.

The operation signals from the first oscillator circuit 20 and the second oscillator circuit 25 are provided to switch over a first switch SW1 and a second switch SW2, respectively. An inverter 33 is connected between the first switch SW1 and the frequency change-over switches 31 and 32. Thus, while the frequency change-over switch 31 is ON, the switches SW1 and SW2 are turned on and off alternately in response to the operation signal of the frequency f1 produced by the first oscillator circuit 20. When the frequency change-over switch 32 is ON, the switches SW1 and SW2 are turned on and off alternately in response to the operation signal of the frequency f2 produced by the second oscillator circuit 25.

The detector 40 has a detection electrode pair 41, which is provided in a fuel passage of the vehicle. The electrodes of the detection electrode pair 41 face each other to form a capacitor. The electrostatic capacity of the detection electrode pair 41 is detected to measure the concentration of ethanol. A leak resistance Rp exists as a factor that impedes the measurement. This leak resistance Rp varies in accordance with the impurities, and is considered to be connected in parallel to the electrodes of the detection electrode pair 41.

The positive terminal of the detection electrode pair 41 is connected to the inverting input terminal of an operational amplifier 43 through a coupling capacitor 42 and the switch SW1. A capacitor 44 and a gain resistor Rg are connected in parallel between the output terminal and the inverting terminal of the operational amplifier 43. Resistors 45 and 46 are connected in series between the voltage source 12 and the ground. The junction between the resistors 45 and 46 is connected to the non-inverting input terminal of the operational amplifier 43. The positive terminal and the negative terminal of the detection electrode pair 41 are grounded through the switch SW2 and directly, respectively.

The output terminal of the operational amplifier 43 is connected to the non-inverting input terminal of an operational amplifier 48 through a resistor 47. This non-inverting input terminal is grounded through a capacitor 49. As a result, the output voltage of the operational amplifier 43 is applied to the non-inverting input terminal of the operational amplifier 48 as a smoothed or averaged detection voltage Va. The output terminal and the inverting input terminal of the operational amplifier 48 are connected to each other. The output voltage of the operational amplifier 48 is applied to the AC coupler circuit 60 as the detection voltage.

The reference voltage generator circuit 50 includes resistors 51 to 53 and an operational amplifier 54. The resistors 51 and 52 are connected in series between the voltage source 12 and the ground to produce a reference voltage Vr (2.5V) by dividing the source voltage Vcc. The non-inverting input terminal of the operational amplifier 54 is connected to the junction between the resistors 51 and 52. The inverting input terminal and the output terminal of the operational amplifier 54 are connected to each other and grounded through the resistor 53. Thus, the operational amplifier 54 operates as a buffer that outputs the reference voltage Vr.

The AC coupler circuit 60 includes a coupling capacitor 61 and a resistor 62 for AC-coupling the operational amplifier 48 and the amplifier circuit 70. The amplifier circuit 70 includes an operational amplifier 71 and resistors 72 and 73. The output terminal of the operational amplifier 48 is connected to the non-inverting input terminal of the operational amplifier 71 through the capacitor 61. The junction between the capacitor 61 and the non-inverting input terminal of the operational amplifier 71 is connected to the output terminal of the operational amplifier 54. The output terminal of the operational amplifier 71 is connected to the inverting input terminal of the operational amplifier 71 through the resistor 72. The output terminal of the operational amplifier 54 is also connected to the inverting input terminal of the operational amplifier 71 through the resistor 73. Thus, the amplifier circuit 70 amplifies a voltage Vb with respect to the reference voltage Vr, and produces an amplified voltage Vc which is applied to the terminal AD2 of the microcomputer 80.

The microcomputer 80 is supplied with the source voltage Vcc, The microcomputer 80 A/D-converts the output voltage Vc of the amplifier circuit 70 and calculates a change of the output voltage Vc. The output terminal 11 is connected to an electronic control unit (ECU not shown) for engine control. The output terminal of the operational amplifier 48 is connected to the terminal AD1 of the microcomputer 80 thereby to detect any abnormality in the output voltage. For example, an alarm process may be executed, when the output voltage exceeds a predetermined measurement range by operating the circuits at one frequency (e.g., f1). Thus, the microcomputer 80 operates as a conductivity measuring section and an abnormality signal outputting section.

Figure 2A:
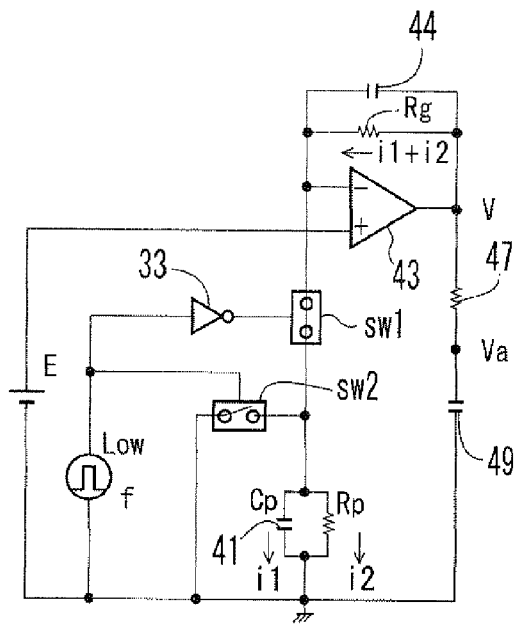
FIGS. 2A and 2B are circuit diagrams showing basic operations of the first embodiment.
Figure 2B:
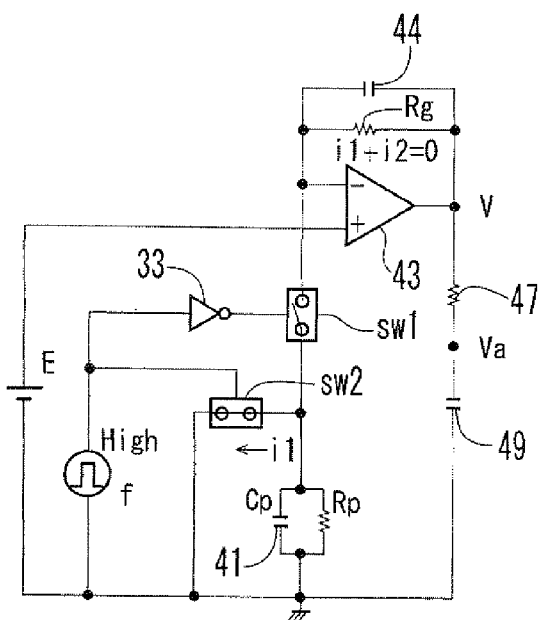

The basic operation of the alcohol concentration measuring device 1 configured as above is described next with reference to FIGS. 2A, 2B and 3. The circuit example shown in FIGS. 2A and 2B is similar to that of FIG. 1 except that no capacitor 42 is connected to the detection electrode pair 41. The first oscillator circuit 20 and the second oscillator circuit 25 produce respective operation signals of the frequencies f1 and f2 to alternately turn on and off the switches SW1 and SW2 at either one of the frequencies f1 and f2.

When the operation signal is at the low level, as shown in FIG. 2A, the switch SW1 is turned on and the switch SW2 is turned off. The operational amplifier 43 operates to equalize the potentials of its inverting and non-inverting input terminals, so that a current i1+i2 flows in the gain resistor Rg due to the source voltage E. Here, the currents flowing in the detection electrode pair 41 and the leak resistance Rp are indicated as i1 and i2, respectively.

Figure 3:
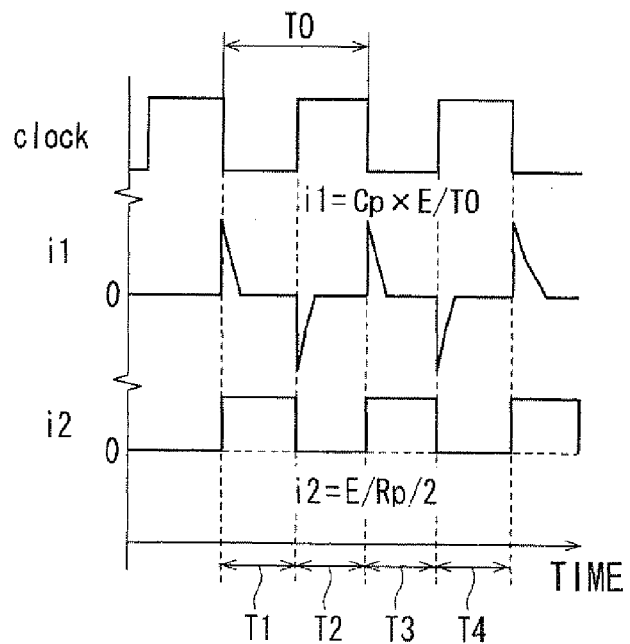
FIG. 3 is a time chart showing currents that flow in a detection electrode pair and a leak resistance.

In this instance, as shown in each period T1 and T3 of FIG. 3, the current i1 flowing in the detection electrode pair 41 rises and falls to zero when the detection electrode pair 41 is fully charged. The current i2 flowing in the leak resistance Rp is maintained at a fixed value. In actuality, the current i2 rises with some delay relative to the current i1 because the sum of currents i1+i2 is fixed. In FIG. 3, however, both currents i1 and i2 are shown as rising at the same time for simplicity.

When the operation signal is at the high level, as shown in FIG. 2B, the switch SW1 is turned off and the switch SW2 is turned on. In this instance, the positive side of the detection electrode pair 41 is grounded. Therefore, the charge of the detection electrode pair 41 having been charged through the switch SW1 is discharged through the switch SW2, and the current i1 flows in the detection electrode pair 41 in the direction reverse to the time of charging.

That is, as shown in each period T2 and T4 of FIG. 3, the current i1 flowing in the detection electrode pair 41 falls (changes in the opposite direction) and returns to zero when the detection electrode pair 41 is fully discharged. The current i2 flowing in the detection electrode pair 41 is maintained at zero.

When each of the switches SW1 and SW2 are turned on and off alternately at a frequency f, the average value of the current i2 is defined as the following equation (1).

$$i2 = 0.5 \times E/Rp \tag{1}$$

The charge accumulated in the detection electrode pair 41 is defined as the following equation (2), in which the capacitance of the detection electrode pair 41 is Cp.

$$\Delta Q = Cp \times E \tag{2}$$

The average of the current i1 is a time differentiation of the charge. Therefore, the current i1 is defined as the following equation (3) by using the equation (2). Here, T0 is a period of the operation signal, which is in inverse proportion to the frequency f of the operation signal.

$$i1 = \Delta Q/T0 = Cp \times E/T0 = Cp \times E \times f \tag{3}$$

The output voltage V is defined as the following equation (4) by using the equations (1) and (3).

$$\begin{aligned} V &= E + (i1 + i2) \\ &= E + Rg \times (Cp \times E/T0 + 0.5 \times E/Rp) \\ &= E(1 + 0.5 \times Rg/Rp + f \times Rg \times Cp) \end{aligned} \tag{4}$$

According to the equation (4), the output voltage V does not substantially change if the leak resistance Rp is close to infinity. That is, the concentration of ethanol is measured with high precision. However, if the leak resistance Rp becomes smaller due to inclusion of more impurities, the output voltage V will change with Rg/Rp and have more error.

According to the first embodiment, the switches SW1 and SW2 are turned on and off by either one of two operation signals of the frequencies f1 and f2 of the first oscillator circuit 20 and the second oscillator circuit 25, and the difference in the output voltages V(f1) and V(f2) of the operational amplifier 43 is calculated as the following equation (5). The output voltages V(f1) and V(f2) are produced, when the switches SW1 and SW2 are operated at the frequencies f1 and f2, respectively.

$$V(f1) - V(f2) = E \times (f1 - f2) \times Rg \times Cp \tag{5}$$

Thus, the influence of the leak resistance included in the respective output voltages V(f1) and V(f2) is cancelled out, and as a result the electrostatic capacity Cp of the detection electrode pair 41 is measured as a function of the difference between the two output voltages.

Figure 4:
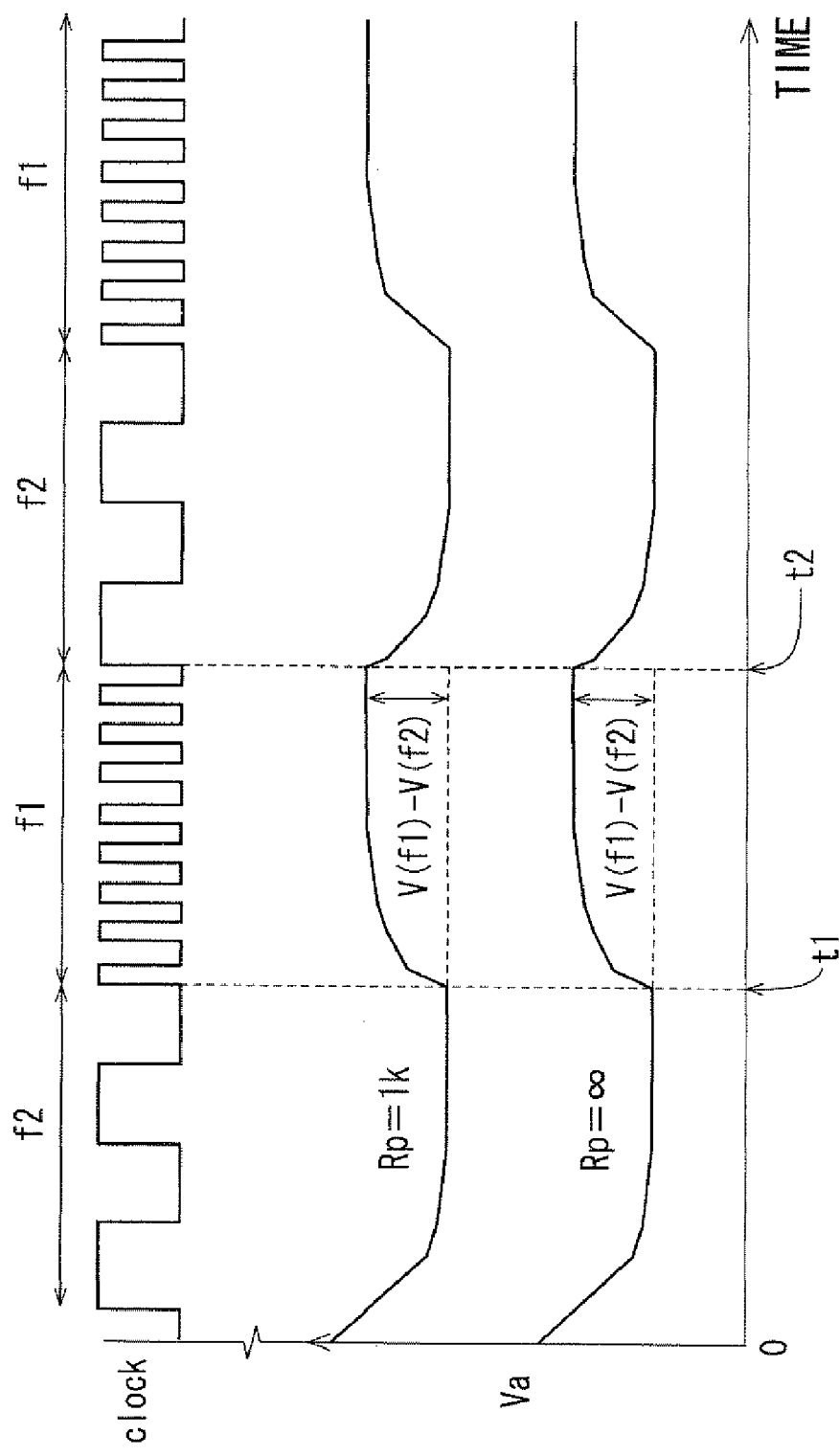
FIG. 4 is a time chart showing a detection output voltage.

The output voltage V of the operational amplifier 43 is averaged by the resistor 47 and the capacitor 49 forming a smoothing circuit, and the voltage Va thus smoothed is applied to the operational amplifier 48 as the detection voltage. This voltage Va changes as shown in FIG. 4, when the switches SW1 and SW2 are turned on and off first at the frequency f2 until time t1 and then by the first frequency f1 until time t2. At the times t1 and t2, the voltage Va is converged and does not change. The time of this switching of frequency, that is, period of operating the switches SW1 and SW2 by either one of the frequencies f1 and f2, is controlled by the microcomputer 80 by turning on the switches 31 and 32 alternately based on the change of the voltage Va.

As understood from the equation (4), the voltage Va becomes larger as the leak resistance Rp becomes smaller. In FIG. 4, two voltages Va are shown exemplarily, assuming that the leak resistance Rp is infinity ($\infty$) and 1 k$\Omega$. Although the difference between the output voltages V(f1) and V(f2) is not affected by the leak resistance Rp, the voltage Va itself is still influenced by the leak resistance Rp. In the worst case, the voltage Va may exceed the normal measurable range.

According to the first embodiment, therefore, the coupling capacitor 42 is provided as shown in FIGS. 1, 5A and 5B so that the positive terminal of the detection electrode pair 41 is AC-coupled. The circuit shown in these figures operate basically in the same manner as described with reference to FIGS. 2A and 2B. However, in this instance, the average value of the current i2 becomes one half of the current i2, which flows in the case of no coupling capacitor 42 (FIGS. 2A and 2B). Thus, the influence of the leak resistance Rp is reduced to one half as will be understood from the equation (4).

Figure 7:
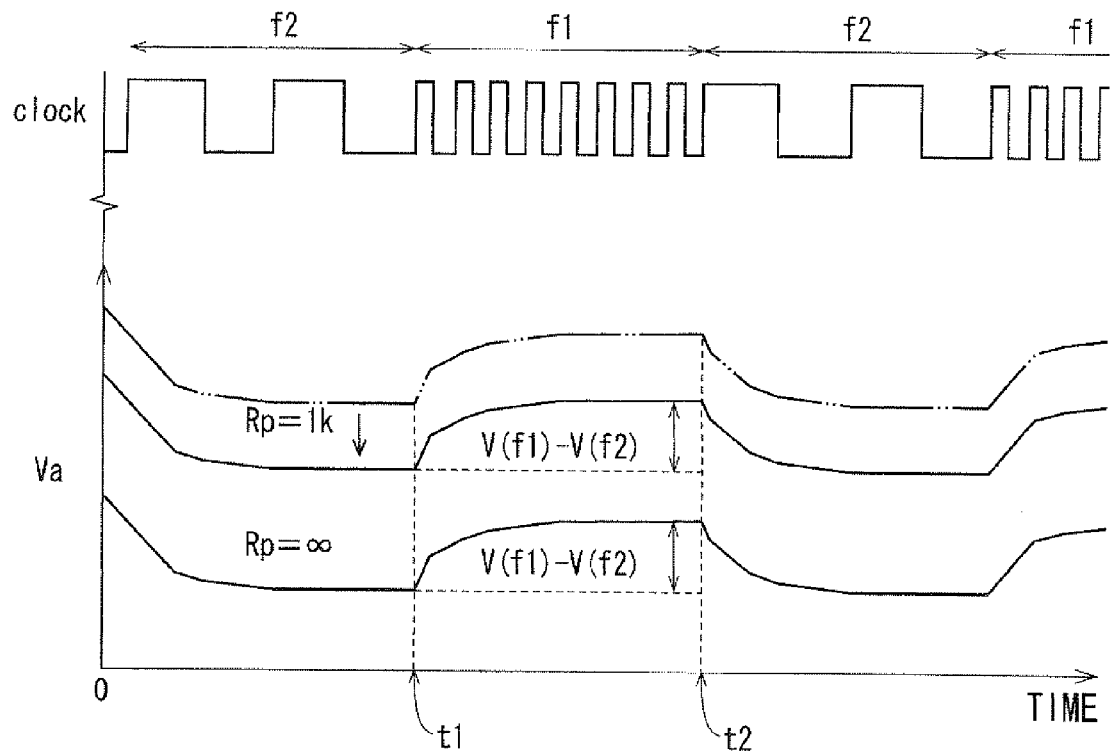
FIG. 7 is a time chart showing a detection output voltage.

More specifically, as shown in FIG. 7, the voltage Va is reduced as shown by the solid line by the coupling capacitor 42 under the condition that the leak resistance Rp is 1 k$\Omega$. The voltage Va, which is produced under the same leak resistance Rp (1 k$\Omega$) in FIG. 2A, is shown by the two-dot dash line. Further, with the coupling capacitor 42, the electric charge is suppressed from being accumulated only at one terminal of the detection electrode pair 41, and as a result the detection electrode pair 41 is protected from electric corrosion.

Figure 8:
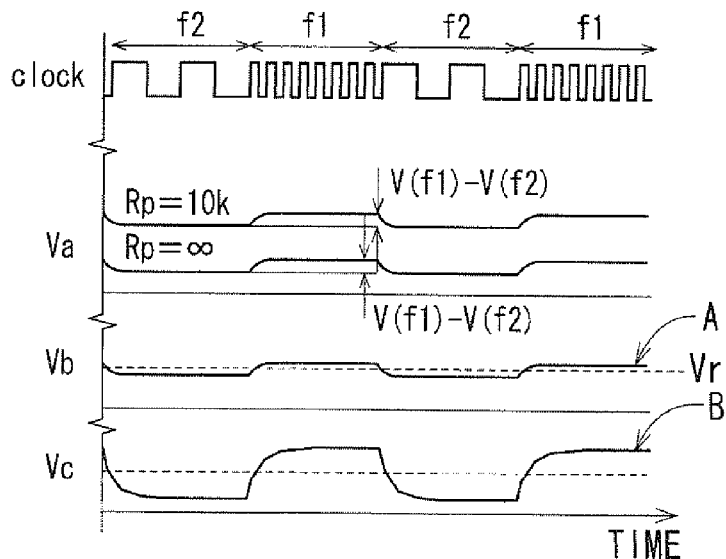
FIG. 8 is a time chart showing a detection output voltage amplified with respect to a reference voltage.

This voltage Va is corrected to the voltage Vb by the operational amplifier 48, the reference voltage generator circuit 50 and the AC coupler circuit 60. The voltage Vb has, as a reference, the reference voltage Vr (2.5V) produced by the reference voltage generator circuit 50. That is, the voltage Vb changes with respect to the reference voltage Vr as indicated as characteristic A in FIG. 8. The voltage Vb is amplified by the amplifier circuit 70 and results in the amplified voltage Vc as indicated by the characteristic B in FIG. 8.

In the first embodiment, the switches SW1 and SW2 operate as a switching section, and the oscillator circuits 20, 25, change-over switches 31, 32 and the microcomputer 80 operate as an operation signal outputting section. The operational amplifier 43, the gain resistor Rg, the capacitor 44, the resistors 45, 46, 47 and the capacitor 49 operate as a measured value outputting section. The resistor 47 and the capacitor 49 operate as a smoothing section. The reference voltage generator circuit 50, the AC coupler circuit 60, the amplifier circuit 70 and the microcomputer 80 operate as a reference voltage generating section, an AC-coupling section, an amplifying section and a difference calculating section, respectively.

As described above, the alcohol concentration measuring device 1 according to the first embodiment can measure the ethanol concentration precisely without being affected by the leak resistance Rp. Particularly, the coupling capacitor 42 can reduce the detection voltage Va as shown in FIG. 7 the range of measurement can be widened comparatively. The electric charge is accumulated at both electrodes of the detection electrode pair 41 alternately, and hence the electric corrosion of the detection electrode pair 41 can be suppressed. The negative electrode of the detection electrode pair 41 is directly grounded, the charging and discharging circuits can be formed in the simple configuration by the switches SW1 and SW2. The switches SW1 and SW2 can be protected from being damaged by static electric charge and from being erroneously operated by electromagnetic waves.

(Second Embodiment)

Figure 9:
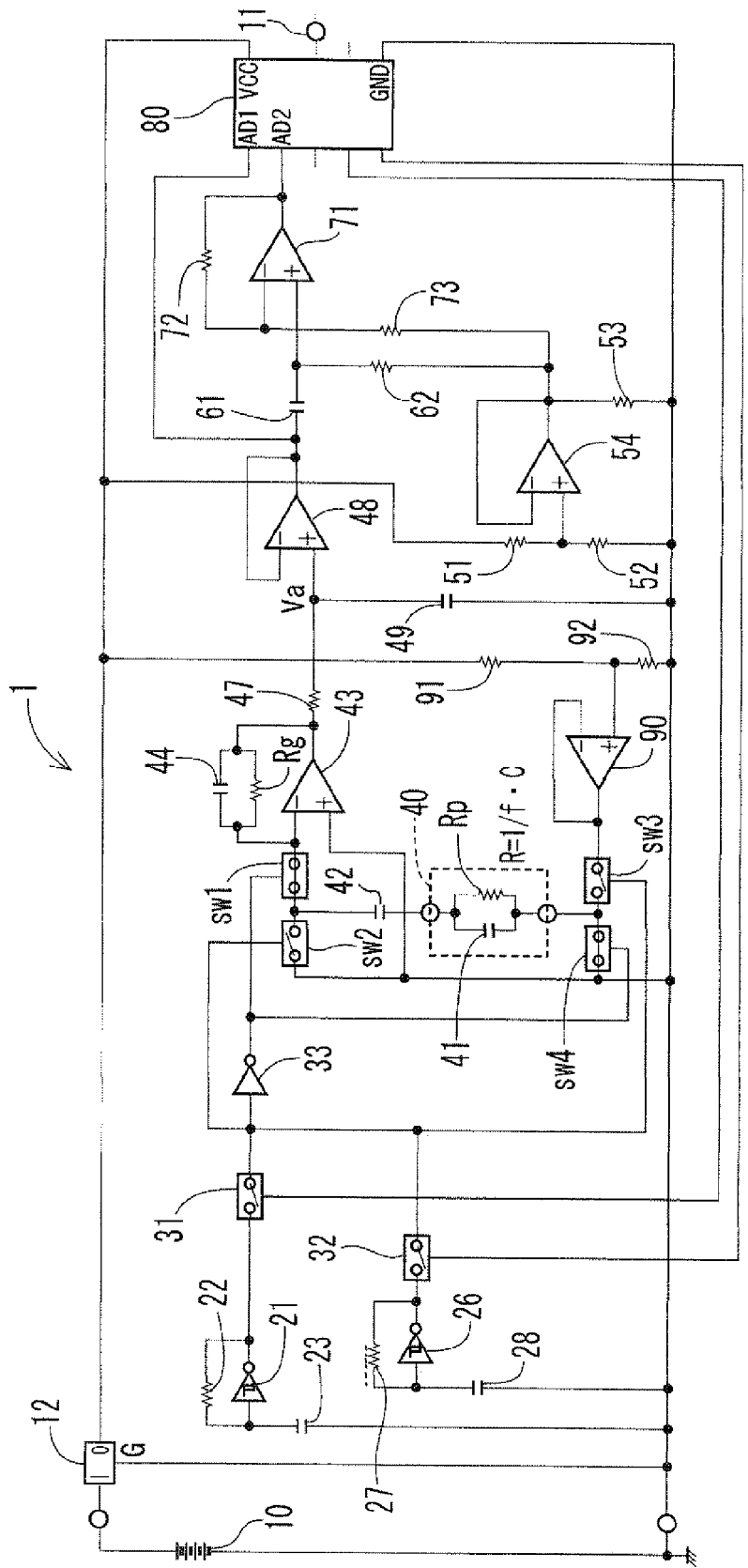
FIG. 9 is a circuit diagram showing an alcohol concentration measuring device according to the second embodiment of the present invention.

In the second embodiment, as shown in FIG. 9, the detection electrode pair 41 of the detector 40 is connected differently from the first embodiment.

The alcohol concentration measuring device 1 has resistors 91 and 92 connected in series between the source voltage Vcc and the ground. The junction between the resistors 91 and 92 is connected to the non-inverting input terminal of an operational amplifier 90. The output terminal and the inverting input terminal of the operational amplifier 90 are connected to each other. The output terminal of the operational amplifier 90 is connected to the inverting input terminal of the operational amplifier 43 through a third switch SW3 and a fourth switch SW4 as well as the switches SW1 and SW2. The switches SW2 and SW4 are grounded and connected to the non-inverting input terminal of the operational amplifier 43.

With this crawl configuration, the output voltage V is defined as the following equation (6).

$$V = E(Rg \times f \times Cp + 0.25 \times Rg/Rp) \tag{6}$$

This equation (6) does not have a constant 1 in the bracketed term in comparison with the equation (4). Therefore, the measurable range can be widened, although two more switches SW3 and SW4 are needed in comparison with the first embodiment.

(Third Embodiment)

Figure 10:
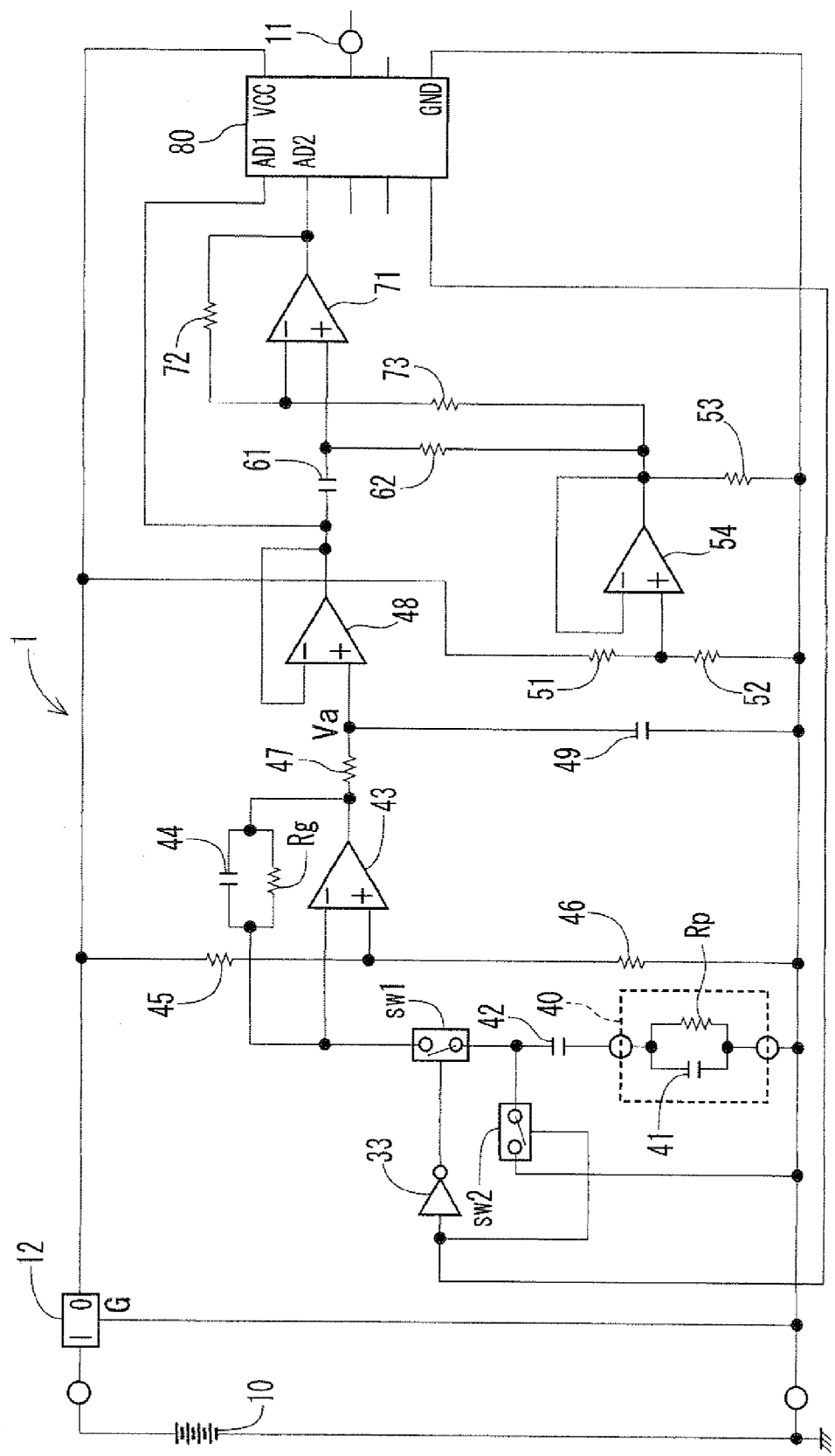
FIG. 10 is a circuit diagram showing an alcohol concentration measuring device according to the third embodiment of the present invention.

In the third embodiment, as shown in FIG. 10, the first oscillator circuit 20 and the second oscillator circuit 25 of the first embodiment are not provided.

The microcomputer 80 is programmed to produce the operation signals of the frequencies f1 and f2, thus operating as the operation signal outputting section. Thus, not only the oscillator circuits but also the frequency change-over switches 31 and 32 are not necessitated, thus simplifying the circuit configuration and reducing costs of the alcohol concentration measuring device 1.

(Fourth Embodiment)

Figure 11:
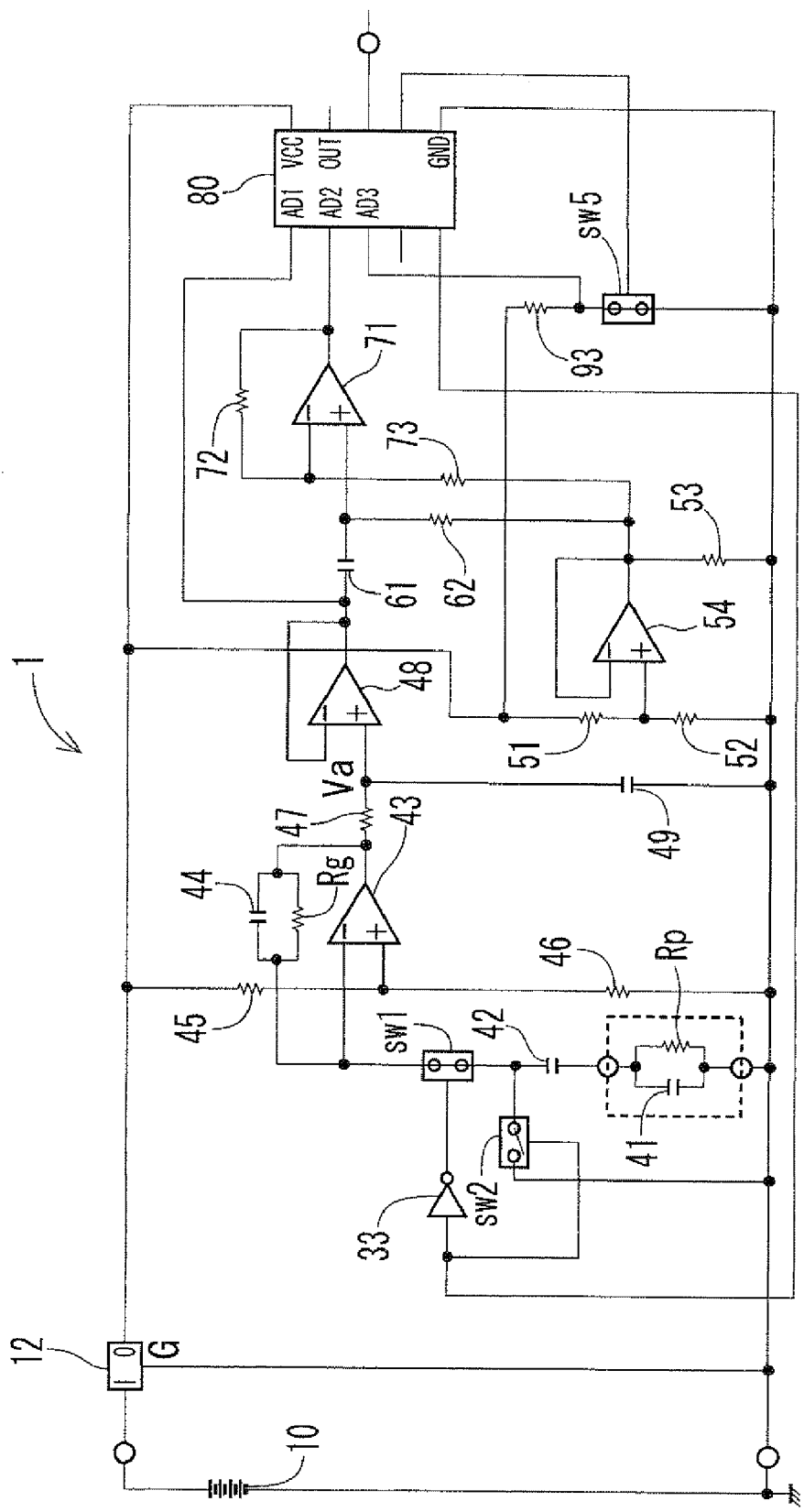
FIG. 11 is a circuit diagram showing an alcohol concentration measuring device according to the fourth embodiment of the present invention.

In the fourth embodiment, as shown in FIG. 11, the alcohol concentration measuring device 1 is configured without the oscillator circuit circuits as in the third embodiment. However, the switch-on resistance of the switches SW1 and SW2 are measured.

A resistor 93 and a switch SW5 are connected in series between the voltage source 12 and the ground. The switch SW5 is controlled by the microcomputer 80. The junction between the resistor 93 and the switch SW3 is connected to the input terminal AD3 of the microcomputer 80. The switch SW3 is preferably provided with other switches SW1, SW2, etc. in a single package. The microcomputer 80 is programmed to measure the switch-on resistance of the switch SW5 based on the voltage applied to the terminal AD3 by turning on the switch SW5. The microcomputer 80 uses this measured switch-on resistance of the switch SW5 as the switch-on resistance of the other switches SW1 and SW2, and corrects the output voltage by this switch-on resistance. Thus, the microcomputer 80 operates as a switch-on resistance measuring section.

In the microcomputer 80, the influence of the switch-on resistance is compensated for in the following manner.

Figure 12:
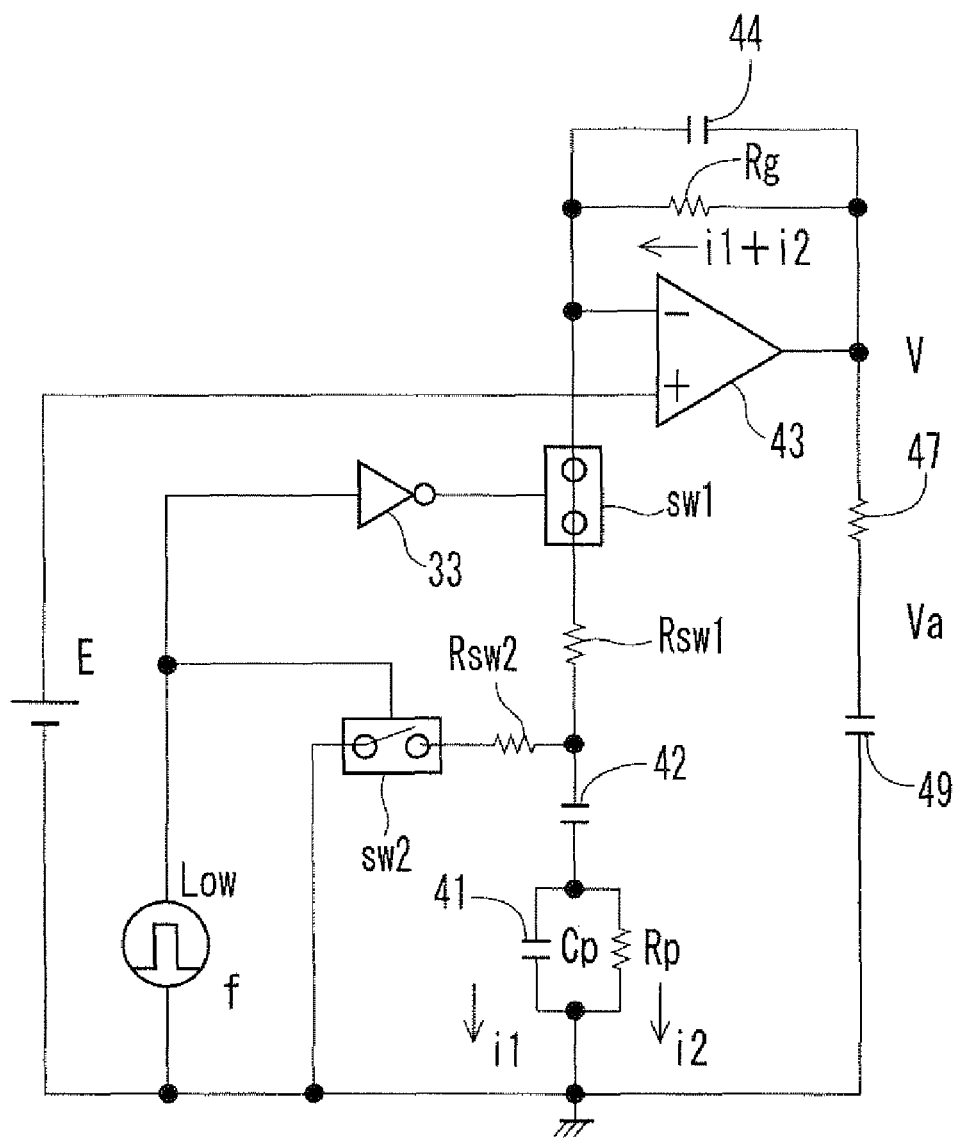
FIG. 12 is a circuit diagram showing a case, in which a switch-on resistance is considered.

As shown in FIG. 12, the switch-on resistance Rsw1 of the first switch SW1 is assumed to be connected in series with the switch SW1, and the switch-on resistance Rsw2 of the second switch SW2 is assumed to be connected in series with the switch SW2. The switch-on resistances Rsw1 and Rsw2 are assumed to be equal to each other.

The voltage V is defined in the following equation (7).

$$\begin{aligned} V &= E + Rg \times (i1 + i2) \\ &= E + Rg \times \left\{ \begin{array}{l} 0.25 \times E/(Rp + Rsw1) + Cp \times \\ f \times E \times Rp^2/(Rp + Rsw1)^2 \end{array} \right\} \end{aligned} \tag{7}$$

The difference between the voltages V(f1) and V(f2) produced when operated at the frequencies f1 and f2 is defined as the following equation (8) by using the equation (7).

$$V(f1) - V(f2) = E \times (f1 - f2) \times Rg \times Cp \times Rp^2/(Rp + Rsw1)^2 \tag{8}$$

The static electrostatic capacitance Cp of the detection electrode pair 41 is calculated from equation (8), and then the leak resistance Rp is calculated from the voltage V(f1) or V(f2). As a result, the compensation coefficient is calculated as $Rp^2/(Rp+Rsw1)^2$.

Since the influence of the switch-on resistances Rsw1 and Rsw2 can be compensated for, the fourth embodiment is advantageous when the leak resistance Rp is very small.

(Fifth Embodiment)

Figure 13:
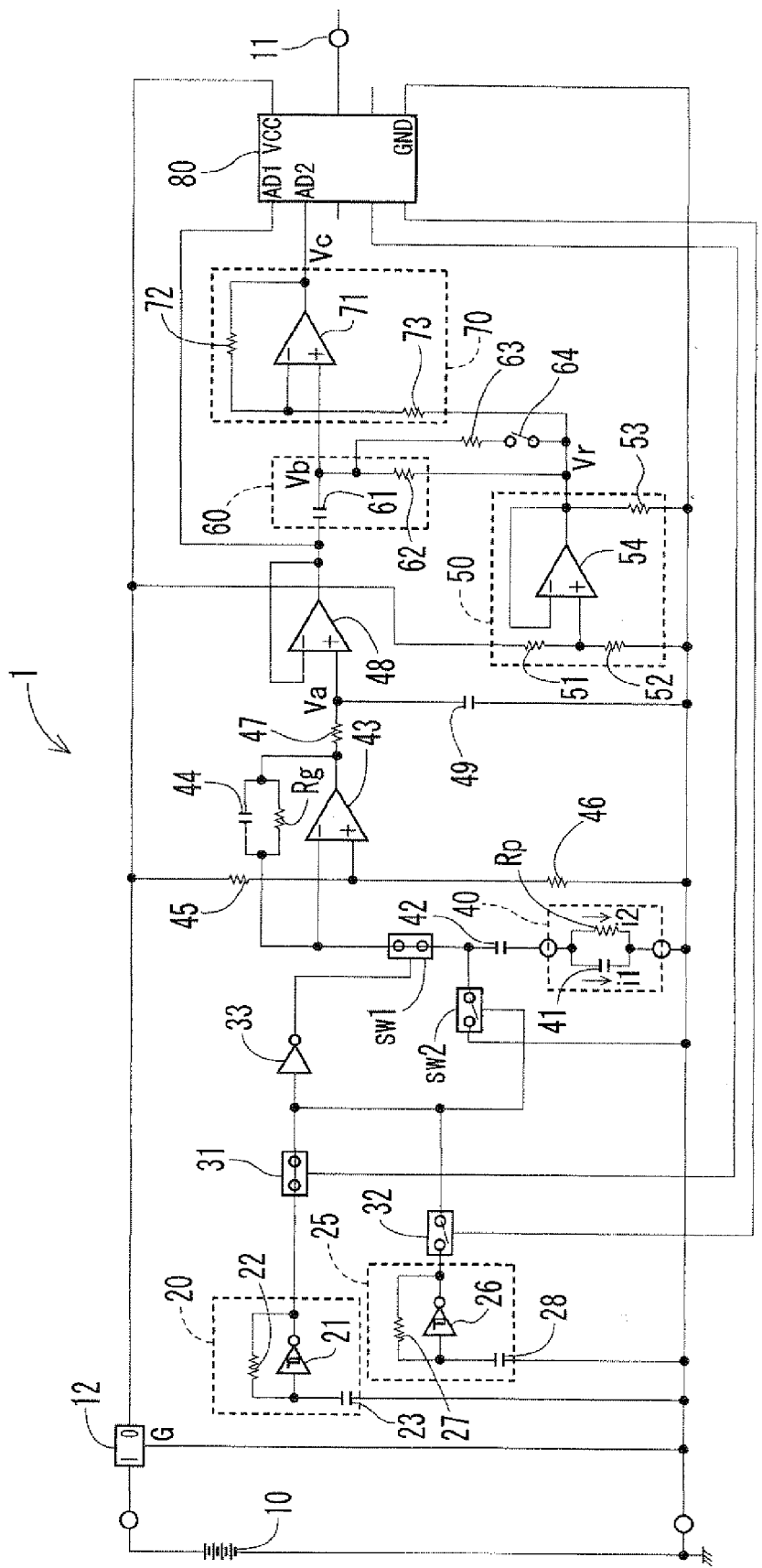
FIG. 13 is a circuit diagram showing an alcohol concentration measuring device according to the fifth embodiment of the present invention.

In the fifth embodiment, as shown in FIG. 13, a circuit is added to the AC coupler circuit 60 so that the electric charge of the capacitor is adjusted in a short time.

As described above, the detection voltage Va is corrected to the voltage Vb by the operational amplifier 48, the reference voltage generator circuit 50 and the AC coupler circuit 60 by using the reference voltage Vr as the reference. The voltage Vb is amplified to the voltage Vc by the amplifier circuit 70. Thus, the AC component of the voltage Vb is amplified, and hence the measured result can be produced with high precision.

For producing the voltage Vb, which varies around the reference voltage Vr, the electric charge of the capacitor 61 of the AC coupler circuit 60 need be adjusted by the reference voltage Vr. It takes some time, from several seconds to tens of several seconds, until capacitor 61 is charged through the resistor 62.

According to the fifth embodiment, therefore, a resistor 63 and a switch 64 are connected in parallel to the resistor 62 of the AC coupler circuit 60. The resistor 63 has a resistance, which is far smaller than that of the resistor 62. The switch 64 may be a FET.

The switch 64 is controlled by the microcomputer 80 to turn on periodically in timed relation with the measurement. The switch 64 is kept turned on for a period (e.g., 10 ms, 20 ms, etc. but less than 100 ms), which is required to charge the capacitor 61. In this period, the capacitor 64 is charged by the reference voltage Vr, and hence the voltage Vb of the AC coupler circuit 60 instantaneously changes around the reference voltage Vr within 100 ms. That is, the reference voltage Vr corresponds to a center voltage of the voltage Vb.

The center voltage is a voltage, around which the voltage Vb changes, and changes as indicated by a dotted line in FIG.

14 if operated alternately at the frequencies f1 and f2. The center voltage is a voltage, which is intermediate of the variation of the voltage Vc.

Figure 14:
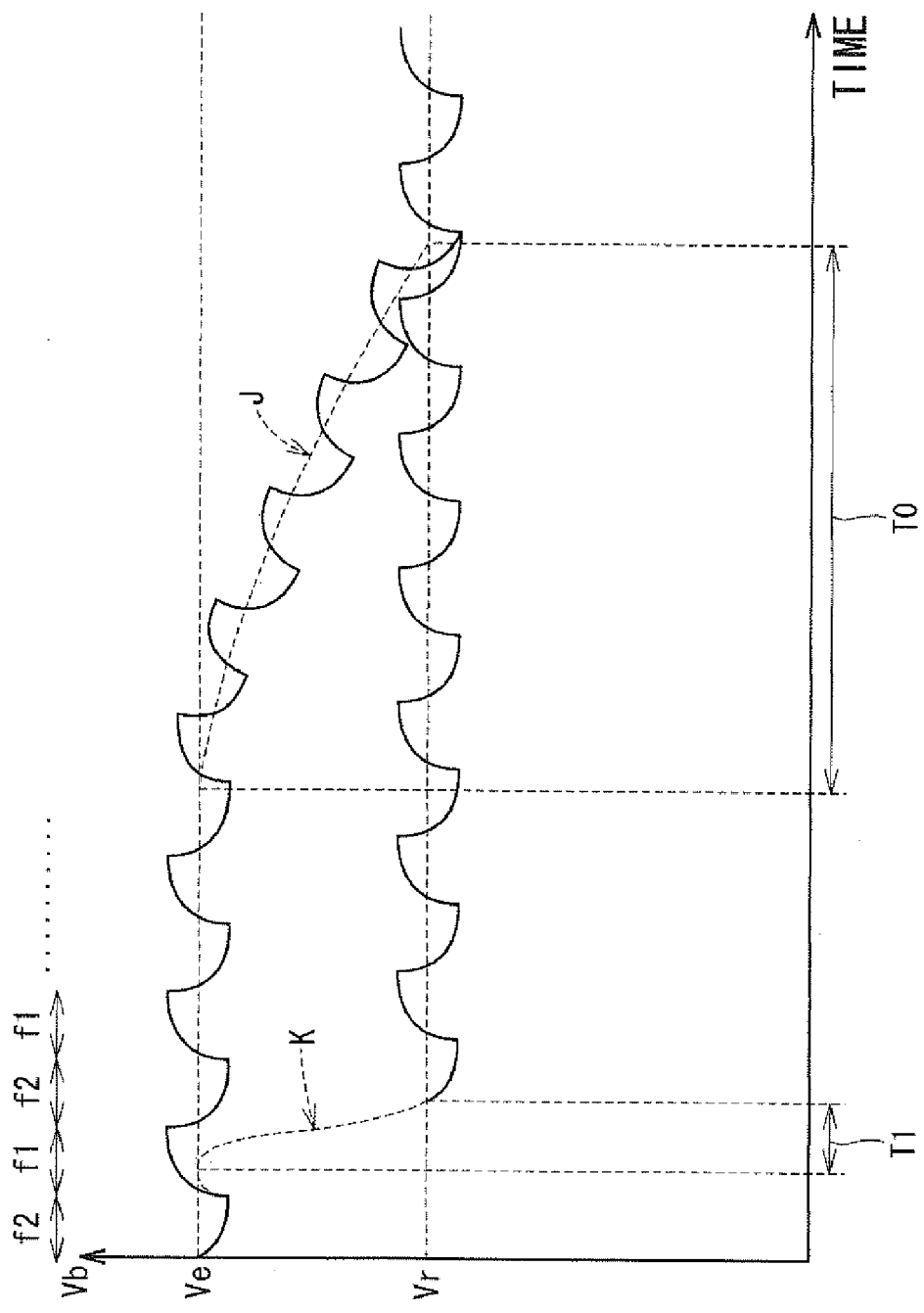
FIG. 14 is an explanatory diagram schematically showing changes of a center voltage, which corresponds to changes in the measured alcohol concentration.

As shown in FIG. 14, the center voltage, around which the voltage Vb changes, is a voltage Ve for some time because of the leak resistance Rp, and later is decreased to the reference voltage Vr.

Since the capacitor 61 is charged through the resistor 62 normally, the center voltage is changed gradually from Ve to Vr in a period T0 of several seconds to tens of several seconds as indicated by the characteristic J.

In the fifth embodiment, however, the resistor 63 and the switch 64 are connected in parallel to the resistor 62. Since the resistance of the resistor 63 is far smaller than that of the resistor 62, the center voltage changes to the reference voltage Vr as shown by the characteristic K within a short period (10 ms, 20 ms, etc.) shorter than 100 ms.

As a result, even if the influence of the leak resistance Rp is large, the voltage Vb changing around the reference voltage Vr as the center voltage can be produced within a short period of time.

In the fifth embodiment, the resistor 63, switch 64 and the microcomputer 80 operate as an electric charge adjusting section.

The fifth embodiment may be modified in many ways. For example, the switch 64 may be turned on when the ignition switch (not shown) for starting an engine is turned on. With this modification, the measurement can be started before the engine is started even if the influence of the leak resistance Rp is large.

It is likely that the voltage Vb exceeds the measurable range before the center voltage of the voltage Vb converges to the reference voltage Vr. It is therefore possible to produce a third frequency f3, which is intermediate the frequencies f1 and f2, during a period T1 (FIG. 14), in which the switch 64 is kept turned on. Although the voltage Vb rises and falls across the center voltage when the two frequencies f1 and f2 are used, the voltage Vb is made not to change around the center voltage by the intermediate frequency f3. As a result, the voltage Vb is restricted from exceeding the measurable range even under the condition that the electric charge is adjusted.

The adjustment of the electric charge of the capacitor 61 by the resistor 63, the switch 64 and the microcomputer 80 may be adopted in any of the first to the fourth embodiments.

The alcohol concentration measuring device 1 according to the above embodiments may be applied as a methanol concentration measuring device or other liquid concentration measuring device as well.

What is claimed is:

1. A liquid concentration measuring device comprising:
a detection electrode pair including a pair of electrodes facing each other;
a switching section connected to switch charging and discharging of the detection electrode pair;
an operation signal outputting section configured to produce operation signals of a predetermined frequency to control switching operation of the switching section at a predetermined period; and
a measured value outputting section configured to produce a voltage for charging the detection electrode pair through the switching section and to produce a detection voltage corresponding to a static electric capacity of the detection electrode pair as a measured value,
wherein the operation signal outputting section is configured to produce alternately a first operation signal of a first frequency and a second operation signal of a second frequency different from the first frequency for operating the switching section during a first period and a second period, respectively, the first and the second period being determined such that the detection voltage is converged in each period;
wherein the measured value outputting section is configured to produce a first detection voltage and a second detection voltage when the switching section is operated at the first frequency in the first period and the second frequency in the second period, respectively; and
wherein the device further comprises a difference calculating section configured to produce a difference between the first detection voltage and the second detection voltage, which are produced when the frequency for operating the switching section is switched over between the first frequency and the second frequency, and the difference is produced as the measured value.

2. The liquid concentration measuring device according to claim 1, further comprising: an amplifying section configured to amplify the first detection voltage and the second detection voltage.

3. The liquid concentration measuring device according to claim 2, further comprising: a reference voltage generating section configured to produce a reference voltage, wherein the amplifying section is configured to amplify the first detection voltage and the second detection voltage with respect to the reference voltage.

4. The liquid concentration measuring device according to claim 3, further comprising: an AC-coupling section configured to AC-couple the first detection voltage and the second detection voltage to the amplifying section based on the reference voltage.

5. The liquid concentration measuring device according to claim 4, further comprising: a charge adjusting section configured to adjust an amount of charge of a capacitor of the AC-coupling section within a predetermined period.

6. The liquid concentration measuring device according to claim 5, wherein: the charge adjusting section is configured to adjust the amount of charge of the capacitor periodically.

7. The liquid concentration measuring device according to claim 5, wherein: the charge adjusting section is configured to adjust the amount of charge of the capacitor when an ignition switch of an engine is turned on before the engine is started.

8. The liquid concentration measuring device according to claim 5, wherein: the operation signal outputting section is configured to produce a third operation signal of a third frequency in timed relation with a period of adjustment operation of the charge adjusting section, the third frequency being intermediate the first frequency and the second frequency.

9. The liquid concentration measuring device according to claim 1, wherein: the measured value outputting section includes a smoothing section for smoothing the first detection voltage and the second detection voltage.

10. The liquid concentration measuring device according to claim 1, further comprising: a coupling capacitor connected to a positive terminal of the detection electrode pair.

11. The liquid concentration measuring device according to claim 1, wherein: the detection electrode pair has a negative terminal directly grounded.

12. The liquid concentration measuring device according to claim 1, wherein: the measured value outputting section is connected in a crawl configuration to the detection electrode pair.

13. The liquid concentration measuring device according to claim 1, wherein: the operation signal outputting section is configured to alternately produce the first operation signal of the first frequency and the second operation signal of the second frequency periodically.

14. The liquid concentration measuring device according to claim 1, wherein: the operation signal outputting section includes a microcomputer.

15. The liquid concentration measuring device according to claim 1, further comprising: a conductivity measuring section configured to measure a conductivity of the detection electrode pair based on at least one of the first detection voltage and the second detection voltage, wherein a difference between the first detection voltage and the second detection voltage is corrected by the measured conductivity and a predetermined switch-on resistance of the switching section.

16. The liquid concentration measuring device according to claim 15, further comprising: a switch-on resistance measuring section configured to measure the switch-on resistance, wherein the difference is corrected based on the measured switch-on resistance.

17. The liquid concentration measuring device according to claim 1 further comprising: a conductivity measuring section configured to measure a conductivity of the detection electrode pair based on at least one of the first detection voltage and the second detection voltage; and an abnormality signal outputting section configured to produce an abnormality signal when the measured conductivity exceeds a predetermined threshold.

18. A liquid concentration measuring device comprising:
a detection electrode pair including a pair of electrodes facing each other;
a switching section connected to switch charging and discharging of the detection electrode pair;
an operation signal outputting section configured to produce operation signals of a predetermined frequency to control switching operation of the switching section at a predetermined period; and
a measured value outputting section configured to produce a voltage for charging the detection electrode pair through the switching section and to produce a detection voltage corresponding to a static electric capacity of the detection electrode pair as a measured value,
wherein the operation signal outputting section is configured to produce alternately a first operation signal of a first frequency and a second operation signal of a second frequency different from the first frequency for operating the switching section during a first period and a second period, respectively, the second period being determined such that the detection voltage is converged in each period,
wherein the measured value outputting section is configured to produce a first detection voltage and a second detection voltage when the switching section is operated at the first frequency in the first period and the second frequency in the second period, respectively; and
wherein the device further comprises a calculating section configured to subtract the second detection voltage from the first detection voltage, which are produced when the frequency for operating the switched section is switched over between the first frequency and the second frequency, and a result of the subtraction is produced as the measured value.

19. A liquid concentration measuring device comprising:
a detection electrode pair including a pair of electrodes facing each other;
an operation signal outputting section configured to produce a first operation signal in a pulse form of a first predetermined frequency and a second operation signal in a pulse form of a second predetermined frequency, the first predetermined frequency and the second predetermined frequency being different from each other;
a switching section connected to the detection electrode pair to repeat charging and discharging of the detection electrode pair in response to a frequency of an operation signal produced by the operation signal outputting section, the switching section controlling the repeating and discharging by the first operation signal during a first period and the second operation signal during a second period alternately; and
a measured value outputting section configured to produce a voltage for charging the detection electrode pair through the switching section and to produce a detection voltage corresponding to a static electric capacity of the detection electrode pair as a measured value,
wherein the measured value outputting section is configured to produce a first detection voltage and a second detection voltage when the switching section is operated by the first operation signal and the second operation signal, respectively, and
wherein the first period and the second period have time lengths, in which the first detection voltage and the second detection voltage are converged, respectively.

20. The liquid concentration measuring device according to claim 19, further comprising:
a difference calculating section configured to calculate a difference between the first detection voltage and the second detection voltage, which are produced in the first period and the second period, respectively,
wherein the operation signal outputting section is configured to control the first period and the second period in accordance with changes in the first detection voltage and the second detection voltage.

* * * * *